(12) United States Patent
Chen et al.

(10) Patent No.: US 11,445,941 B2
(45) Date of Patent: Sep. 20, 2022

(54) MAPPING CILIARY ACTIVITY USING PHASE RESOLVED SPECTRALLY ENCODED INTERFEROMETRIC MICROSCOPY

(71) Applicant: The Regents of the University of California, Oakland, CA (US)

(72) Inventors: Zhongping Chen, Irvine, CA (US); Youmin He, Irvine, CA (US); Joseph Jing, Irvine, CA (US); Yueqiao Qu, Irvine, CA (US); Andrew Emon Heidari, Irvine, CA (US); Jason Chen, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 405 days.

(21) Appl. No.: 16/780,659

(22) Filed: Feb. 3, 2020

(65) Prior Publication Data
US 2020/0245905 A1    Aug. 6, 2020

Related U.S. Application Data

(60) Provisional application No. 62/800,284, filed on Feb. 1, 2019.

(51) Int. Cl.
*G01B 9/02* (2022.01)
*A61B 5/11* (2006.01)
(Continued)

(52) U.S. Cl.
CPC ............ *A61B 5/1128* (2013.01); *A61B 1/005* (2013.01); *A61B 1/00096* (2013.01);
(Continued)

(58) Field of Classification Search
CPC ............ A61B 1/00006; A61B 1/00009; A61B 1/0638; A61B 1/07; A61B 1/002;
(Continued)

(56) References Cited

U.S. PATENT DOCUMENTS

| 2011/0102802 A1* | 5/2011 | Izatt | G01B 9/0201 356/479 |
| 2016/0367146 A1* | 12/2016 | Boppart | A61B 5/7207 |

(Continued)

*Primary Examiner* — Howard D Brown, Jr.
(74) *Attorney, Agent, or Firm* — Nguyen Tarbet LLC

(57) ABSTRACT

Ciliary motion in the upper airway is the primary mechanism by which the body transports foreign particulate out of the respiratory system. The ciliary beating frequency (CBF) is often disrupted with the onset of disease. Current imaging of ciliary motion relies on microscopy and high speed cameras, which cannot be easily adapted to in-vivo imaging. M-mode optical coherence tomography (OCT) imaging is capable of visualization of ciliary activity, but the field of view is limited. The present invention features the development of a spectrally encoded interferometric microscopy (SEIM) system using a phase-resolved Doppler (PRD) algorithm to measure and map the ciliary beating frequency within an on face region. This novel high speed, high resolution system allows for visualization of both temporal and spatial ciliary motion patterns.

20 Claims, 12 Drawing Sheets
(12 of 12 Drawing Sheet(s) Filed in Color)

(51) Int. Cl.
*G02B 21/00* (2006.01)
*A61B 1/00* (2006.01)
*A61B 1/267* (2006.01)
*A61B 1/06* (2006.01)
*A61B 1/005* (2006.01)
*A61B 5/00* (2006.01)
*G02B 21/36* (2006.01)
*G01B 9/02004* (2022.01)

(52) U.S. Cl.
CPC ...... *A61B 1/00149* (2013.01); *A61B 1/00172* (2013.01); *A61B 1/00177* (2013.01); *A61B 1/063* (2013.01); *A61B 1/267* (2013.01); *A61B 5/0066* (2013.01); *G01B 9/02004* (2013.01); *G01B 9/02041* (2013.01); *G02B 21/0028* (2013.01); *G02B 21/0048* (2013.01); *G02B 21/056* (2013.01); *G02B 21/365* (2013.01)

(58) Field of Classification Search
CPC ... A61B 5/7214; A61B 5/7253; A61B 5/7257; A61B 5/08; A61B 5/1128; A61B 1/00096; A61B 1/00149; A61B 1/00172; A61B 1/00177; A61B 1/005; A61B 1/063; A61B 1/267; A61B 5/0066; G01B 9/02004; G01B 9/02041; G01B 9/02027; G01B 9/02045; G01B 9/02091; G02B 21/0028; G02B 21/0048; G02B 21/0056; G02B 21/365; G01P 3/36

See application file for complete search history.

(56) References Cited

U.S. PATENT DOCUMENTS

| 2017/0105618 | A1* | 4/2017 | Schmoll | G01B 9/02043 |
| 2020/0245905 | A1* | 8/2020 | Chen | G02B 21/0028 |
| 2020/0249008 | A1* | 8/2020 | Chen | G01B 9/02091 |
| 2021/0239450 | A1* | 8/2021 | Hendon | G01B 9/02044 |

* cited by examiner

MAPPING CILIARY ACTIVITY USING PHASE RESOLVED SPECTRALLY ENCODED INTERFEROMETRIC MICROSCOPY

CROSS-REFERENCES TO RELATED APPLICATIONS

This application is a non-provisional and claims benefit of U.S. Provisional Application No. 62/800,284 filed Feb. 1, 2019, the specification(s) of which is/are incorporated herein in their entirety by reference.

STATEMENT REGARDING FEDERALLY SPONSORED RESEARCH OR DEVELOPMENT

This invention was made with government support under Grants No. R01HL-125084 and No. R01HL-127271 awarded by the National Institutes of Health and Grant No. FA9550-17-1-0193 awarded by the Air Force Office of Scientific Research. The government has certain rights in the invention.

BACKGROUND OF THE INVENTION

The human airway serves not only as a passage for oxygen intake, but also as the first line of defense to protect the lungs from harmful foreign particulate. The main defense mechanism is the mechanical clearance of mucus through ciliary activity and regulation of airway surfaces. Specifically, ciliary beat frequency and amplitude are considered the main factors that determine the maximal transportation speed of the mucus from the lower airway to the pharynx, and hence affect the mucociliary clearance rate (MCR). In addition, it was reported that the ciliary beating synchronicity would also contribute to the MCR. Dysfunction of cilia, caused by ciliary defects such as primary ciliary dyskinesia (PCD), virus, toxins, or trauma will usually result in ineffective mucociliary clearance and lead to lung damage. Although the damage caused by ciliary defects such as PCD cannot be fully treated, previous studies indicate that it is possible to maintain sufficient lung function through appropriate respiratory care. Therefore, it is important to monitor the spatial ciliary beat frequency (CBF) and the ciliary beat pattern (CBP) in human airways for disease diagnosis and management.

The traditional procedure to analyze airway ciliary activity involves three steps: sample preparation, recording, and CBF measurement. A biopsy using a cytology brush is usually performed to harvest the ciliated cells from human respiratory tracts for cell culture. Many techniques, based on the photoelectric method and video cameras, were reported to be capable of evaluating ciliary activity. Due to the microscopic nature of ciliary structure and movement, a high resolution and high sensitivity imaging modality is essential to visualize the CBP and beat frequency. Optical microscopy is useful in resolving single cilia movements but sufficient imaging speed is also required to obtain quantitative results of CBF and record the entire beating cycle. This leads to the utilization of high speed digital camera microscopy system. However, conventional digital camera system cannot investigate ciliary functions in-vivo, and thereby diminishes the effectiveness of the measurement in physiological settings.

In order to overcome these limitations and perform in-vivo studies, optical coherence tomography (OCT) was recently applied on ciliary motion imaging, taking advantage of its micron scale resolution, real time imaging capability, and utilization in endoscopic imaging. Given these powerful features, the study of ciliary functions moves from the dish plate to its natural environment, and demonstrates the feasibility of using OCT to investigate ciliary activity in-vivo. Specifically, a high resolution OCT endoscope is inserted into either the respiratory or uterus cavity to perform continuous acquisition at one cross sectional site, so that the intensity fluctuations caused by ciliary activity can be visualized over time. Although CBF can be estimated from the variations in OCT intensity, the synchronicity between different cilia cannot be easily investigated to study CBP.

To further expand the effectiveness of using an OCT system in imaging ciliary activity, a phase resolved Doppler optical coherence tomography (PRD-OCT) technique was used to probe the beating direction and speed of cilia. PRD-OCT is well known for its capability of measuring microscopic particle movement with pico-meter sensitivity, and is proven to be a powerful tool in visualizing accurate ciliary dynamics by providing not only its transient position but also the relative speed and direction of the ciliary beat. In essence, the PRD technique reports displacement information with respect to a reference within an imaging system to the two-dimensional tissue surface, at each pixel location. Therefore, the displacement information reported is about perpendicular to the surface being imaged, i.e., a topography. Therefore, the beating phase of different cilia can be simultaneously monitored to study their synchronicity and beating patterns. In addition, the velocity imaging ability of PRD-OCT also benefits ciliary studies by enhancing the contrast of moving cilia versus other stationary tissue components, and may possibly aid in locating the ciliated area within the entire cavity during in-vivo experiments. However, to visualize spatial-temporal cilia activity using OCT requires a two dimensional beam scan. Because the rate of the spatial scan must be at least two times greater than the CBF for effective measurements according to the Nyquist-Shannon sampling theory, there is a limitation on the number of scanning points, which limits the lateral field of view (FOV).

FIELD OF THE INVENTION

The present invention relates to optical coherence tomography (OCT) systems, devices and methods for imaging ciliary activity. More specifically, the present invention relates to phase resolved swept source spectrally encoded interferometric microscopy (PRD-SS-SEIM) systems devices and methods for real-time imaging of ciliary activity.

DESCRIPTION OF RELATED ART INCLUDING INFORMATION DISCLOSED

See discussion above.

BRIEF SUMMARY OF THE INVENTION

It is an objective of the present invention to provide systems, devices and methods that allow for real-time, in-vivo imaging of ciliary activity, as specified in the independent claims. Embodiments of the invention are given in the dependent claims. Embodiments of the present invention can be freely combined with each other if they are not mutually exclusive.

A spectrally encoded interferometer (SEI) is capable of lateral 2-D imaging with a single axis beam scan, which allows for en face imaging—where the term en face denotes the imaging of superficial features lying within a shallow volume overlying a broad, two-dimensional surface—at a speed comparable with OCT B-Scans.

The present invention features a swept source spectrally encoded interferometric microscopy (SS-SEIM) system to obtain the en face image of cilia beating frequency and pattern—where the term pattern denotes the synchronicity of transport-effectuating motion among cilia within some neighborhood of the imaged tissue surface—at high speed. Without wishing to limit the scope of the present invention, using a swept source laser whose sweep frequency can attain 100 kHz, the system is able to achieve 91 frames per second (fps) over an en face image area up to 1 $mm^2$. This is the first SS-SEIM system to map the spatial-temporal ciliary activity, and opens up the possibility of investigating spatial ciliary beating frequency and pattern in-vivo.

Although prior techniques using OCT are able to visualize in-vivo cilia activity within one cross-sectional image, they have low potential to study the surface dynamic of ciliated tissue due to their limited lateral FOV. Since ciliary activities naturally occur on the surface of the tissues, en face imaging modality is promised to outperform the cross-sectional imaging technique in demands for the visualization of the ciliated tissue surface dynamic. The spectrally encoded imaging technique allows for en face endoscopic imaging inside the cilia lining cavity, and thereby enables spatial mapping of cilia beat frequency and beat pattern. Additionally, the phase resolved algorithm visualizes ciliary activity at pico-meter sensitivity, which is much higher than OCT resolution and thereby provides more accurate measurement of cilia motion than OCT intensity fluctuation does. A prior study reported a spectrometer based spectrally encoded system to visualize vibration, but the spatial resolution of the system (~7 μm) is not enough to resolve ciliary movement. Additionally, recent studies have discovered that the spectrometer-based Doppler is inferior to swept source based in terms of the maximum measurable Doppler velocity. Therefore, the present invention features a phase resolved Doppler swept source spectrally encoded interferometric microscopy (PRD-SS-SEIM) technique to image the real time surface dynamics of ciliated tissue. However, the present invention is not limited to a swept source system. A spectrometer-based system with a broadband light source optionally can also be used to implement PRD-SEIM system.

One of the unique and inventive technical features of the present invention is the co-registration of optical coherence microscopy (OCM) and spectrally encoded interferometric microscopy (SEIM) data using a dichroic mirror. Without wishing to limit the invention to any theory or mechanism, it is believed that the technical feature of the present invention advantageously provides for robust co-registration which guides the SEIM and tunes the distance from the probe to the sample. The design also allows removing of bulk tissue motion from the measurement in order to image and characterize the cilia motion. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

This patent application contains at least one drawing executed in color. Copies of this patent or patent application publication with color drawing(s) will be provided by the office upon request and payment of the necessary fee.

The features and advantages of the present invention will become apparent from a consideration of the following detailed description presented in connection with the accompanying drawings in which.

DETAILED DESCRIPTION OF THE INVENTION

The present invention describes a PRD-SS-SEIM system to provide real time en face displacement images of ciliated tissue.

Figure 1A:
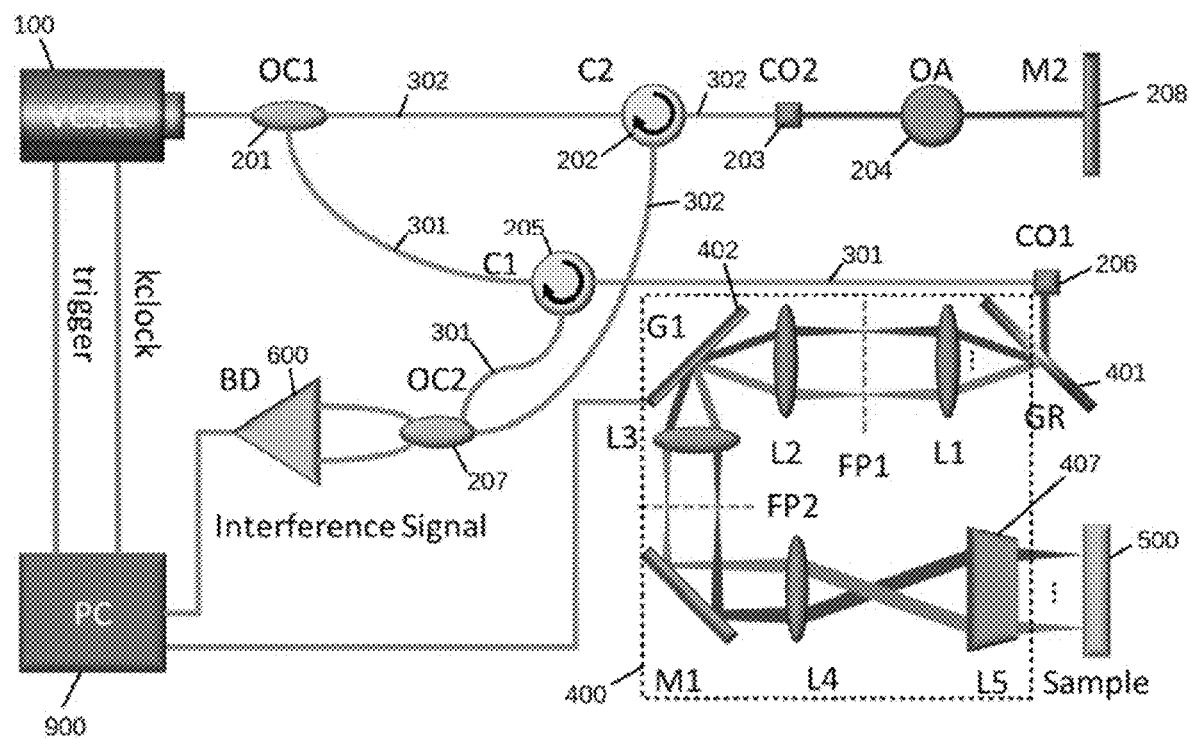
FIG. 1A shows an optical network illustration of the system setup for a swept source spectrally encoded system. The acronym prefixes designating the various optical system components within the figure are decoded as: OC (optical coupler); C (circulator); CO (collimator); OA (optical attenuator); M (mirror); BD (balanced detector): GR (diffraction grating); L (lens); G (galvanometer); FP (focal plane).

FIG. 1A demonstrates an embodiment of the PRD-SS-SEIM system. The embodiment is developed using a vertical-cavity surface-emitting laser (VCSEL) (100) based swept source laser. The center wavelength of the system is 1.3 µm, and the A-line rate is 100 kHz. The lateral resolution and displacement sensitivity are measured to be 1.2 µm and 0.3 nm, respectively; in other words, each pixel in the final graphical output represents a 1.2 µm by 1.2 µm patch of the sample tissue surface; and, the topography of relief due to the motion of cilia above it is resolved to 0.3 nm. The sample arm (301) is configured as a spectrally encoded microscopy, which allows for simultaneous sample illumination with a single mode fiber input. The light in the sample arm (301) is first collimated and diffracted by the diffraction gratings, yielding a line pattern in the fast scan axis as the laser sweeps through its full bandwidth, where the full bandwidth of the laser's sweep corresponds to a wavelength excursion of about +/−50 nm, for a total wavelength excursion of 100 nm, or about 1/13th of the center wavelength of 1.3 µm. (Within this document, the terms fast scan and slow scan refer to the manner in which a two-dimensional array of pixels is serialized. The terms serialized and rasterized can denote the same, identical process, in this context. If each pixel in the two-dimensional array may be indexed by two subscripts i and j as P[i, j], then, when these pixels are serialized, the resulting serial stream of pixels might appear in the following order: { . . . , P[10, 1], P[10, 2], P[10, 3], . . . , P[10, K], P[11, 1], P[11, 2], P[11, 3] . . . }, where K is the array extent in the j-direction. Since the j-index advances more rapidly in this stream, the j-direction is deemed the fast scan axis, while the index i, advancing a 1/K the pace of j, is deemed the slow scan axis. The fast scan can be of either axial direction, i.e., into the sample as a typical A-Scan analogue to ultrasound imaging, or horizontal direction, i.e., a flat line across the surface of the tissue similar to a line scan configuration, depending on the context used). The one-axis, (1-D), galvanometer mirror G1 (402) is used as slow scan driver, which scans the wavelength encoded line of light in its perpendicular direction to produce en face optical imaging. Two optical relays (400) are employed to center the line of light on to the galvanometer mirror (402) and the back focal point of the objective lens, hence ensuring a flat scanning plane on the sample surface. An optical relay is a two-lens configuration that enables an optical path to traverse a region of space without encountering issues of focus, or the optical wavefront's changing radius of curvature with distance from a focal plane. In our context, an optical relay is typically referred to a 4F lens system. An optical relay delivers an optical copy from one location to another. After, a focused line is illuminated on the sample tissue (500) through the high numerical aperture (NA) objective lens (407) L5, where different wavelengths are focused on different locations of the sample based on their diffraction angles. The collected back-scattered light interferes with the light from the reference arm (302) to form an interferogram which is detected by a balanced detector (600), and hence digitized by the PC (900) to generate a raw signal. This embodiment allows for 1 µm lateral resolution, pico-meter displacement sensitivity and a FOV up to 1 $mm^2$. The spatial resolution is much higher than the previous system and the swept-source based system allows for higher limit of Doppler velocity measurement.

The invention further integrates the PRD-OCM and PRD-SEIM technique together to provide co-registered real time cross-sectional and en face imaging of tissue sample (500).

Figure 1B:
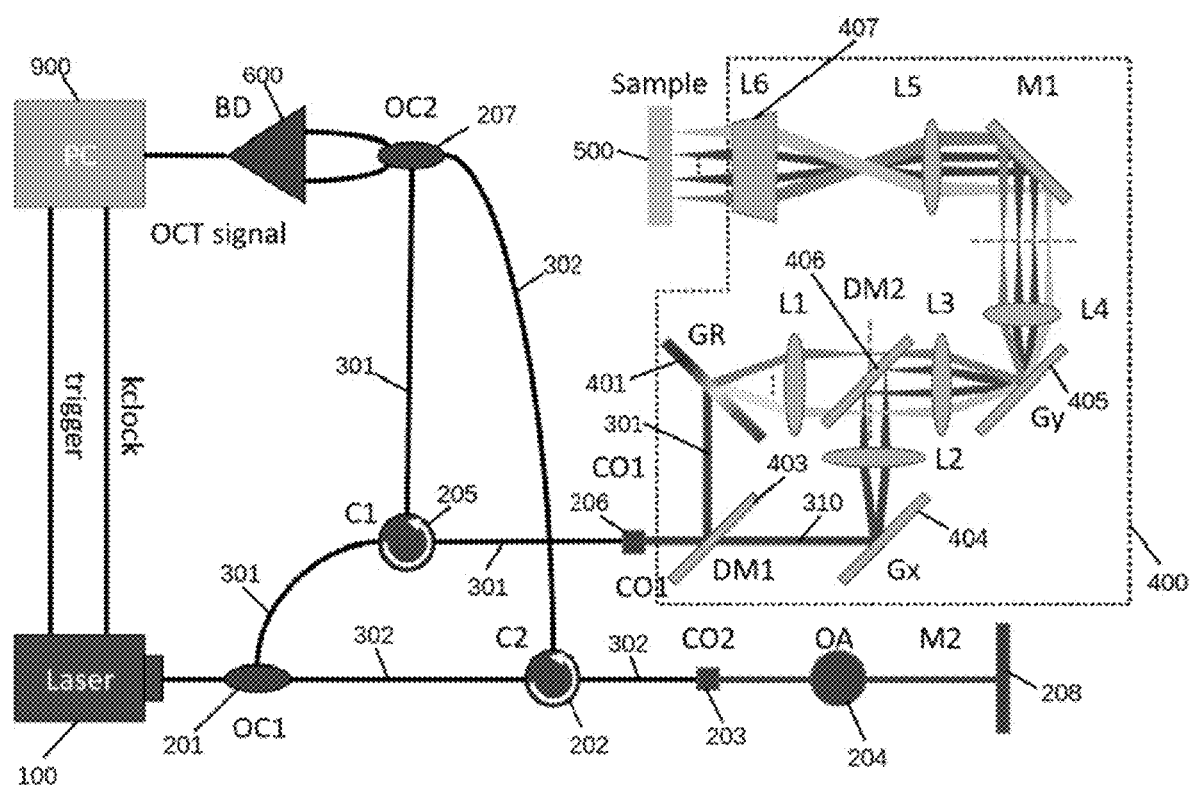
FIG. 1B shows an optical network illustration of the system setup for a spectrally encoded system co-registered with OCT imaging, the purpose of which is to alleviate cilia imaging artifacts due to bulk motion, where the term bulk motion denotes motion common to the entire tissue sample surface. The acronym prefixes designating the various optical system components within the figure are decoded as: OC (optical coupler); C (circulator); CO (collimator); OA (optical attenuator); M (mirror); BD (balanced detector); GR (diffraction grating); L (lens); G (galvanometer); FP (focal plane); DM (dichroic mirror).

FIG. 1B shows a co-registered OCM and SEIM system, where a dichroic mirror DM1 (403) is utilized to split the collimated light into two different pathways, depending on the wavelength. On one way, the light feeds the spectrally encoded sample arm (301) as described two paragraphs prior. On the other, the light goes through a typical OCM sample arm (310). The OCM path way (310) uses a galvanometer mirror Gx (404) to perform the fast axis scan and shares the slow scan galvanometer mirror Gy (405) with the SEIM sample arm (301). Another dichroic mirror DM2 (406) merges the OCM beams into the SEIM pathway by reflecting the wavelengths of OCM beam (310) only. An extra lens L2 is used in the OCM pathway (310) to form optical relays and ensure a flat imaging plane. Since both of OCM beam (310) and SEIM beam (301) were driven by the same slow scan axis, plus proper alignment between their fast scan, we can generate real time co-registered OCM and SEIM data simultaneously. Prior studies have also reported on an OCT and SEIM co-registered system, where they split the beam using optical coupler and merged the beams spatially using a pick off mirror. However, any alteration on the alignment of the pick off mirror may end up as co-registration failure and will compromise the robustness of the co-registration. Therefore, the present invention uses a dichroic mirror (403), of which the alignment does not affect its separation function, to separate the beams spectrally and ensure better robustness than prior art.

The prior art teaches use of the spatial splitting of the beam for coregistration rather than the spectral splitting of the beam because spectral splitting reduces the bandwidth of the beam. This loss of bandwidth sacrifices the axial resolution of the SEIM and thus decreases the information which can be obtained within the tissue being imaged. Surprisingly, despite the loss of bandwidth and sacrifice of axial resolution, the present invention provides for high resolution motion detection.

In some embodiments, the present invention features a microscopic lens system (407). The prior art teaches that use of a microscopic lens (407) system would cause a reduction in the imaging depth capabilities of the system. Surprisingly, even with the loss of imaging depth, the present invention provides for the imaging of non-stationary features.

In some embodiments, the present invention may feature a 2D-scanner setup to improve flattening of the imaging. In other embodiments, the present invention may feature a 4F lens system to improve flattening of the imaging.

The invention may further include a SEIM rigid handheld probe (1200) for in-vivo imaging of ciliary activity inside nasal cavity.

Figure 8:
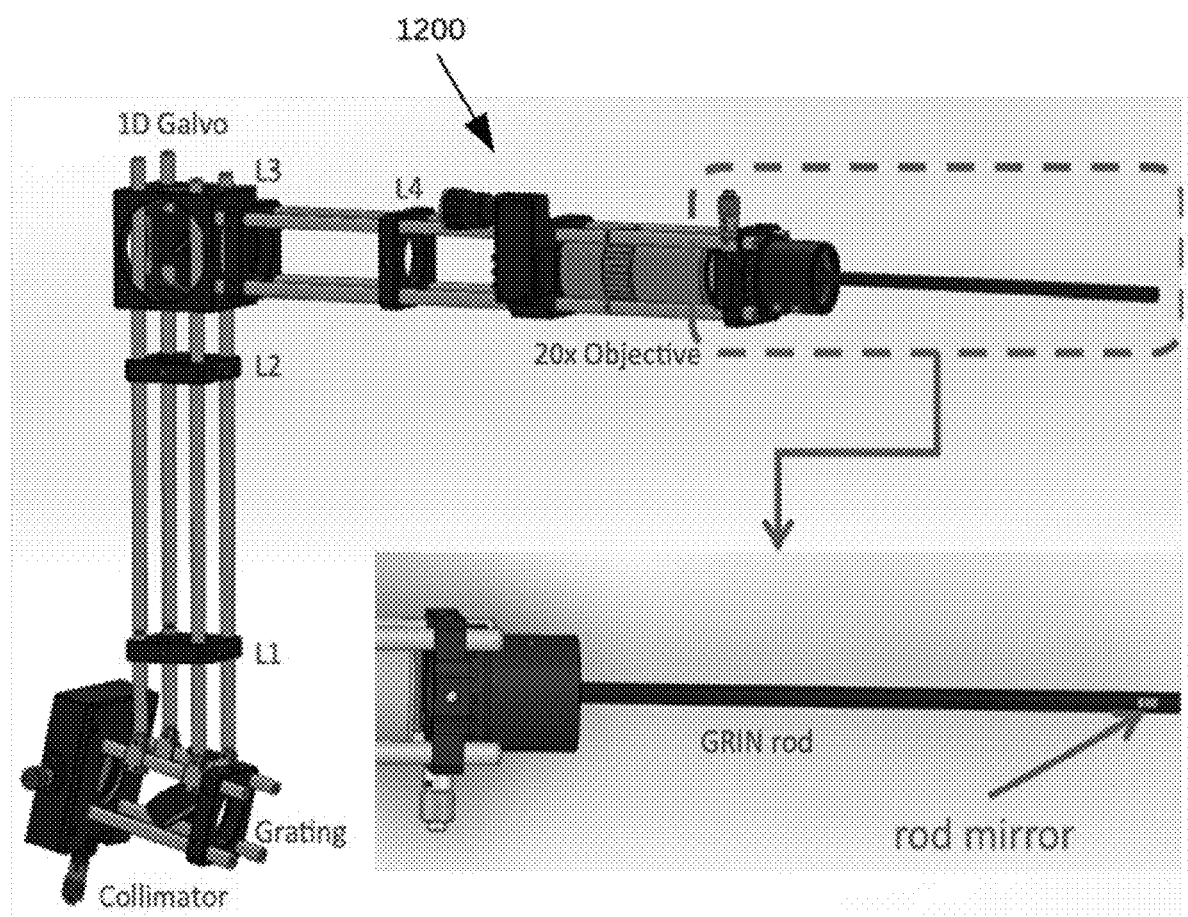
FIG. 8 shows the design of a rigid handheld probe for SEIM imaging.

FIG. 8 demonstrates the design of the rigid handheld probe (1200) for SEIM imaging. The gratings deflect and scan the collimated light along the fast axis, and the galvanometer mirror acts as the slow scan driver. Two pairs of lenses L1-L2 and L3-L4 center the light on the galvanometer mirror and the back focus of the high NA objective, ensuring flat optical illumination on the sample. The gradient-index (GRIN) rod relays the optical illumination to the distal end, allowing for nasal cavity imaging with high NA illumination. A rod mirror will be mount on the distal end to perform side view imaging. A rotational mount, together with a metal tube will hold the GRIN rod and rod mirror assembly and control the region of interest. The rigid tube allows for more stable imaging than flexible probe and thereby minimizes the bulk motion that may overwhelm the ciliary motion. However, a flexible probe optionally may be made by replacing the GRIN rod with a flexible imaging bundle fiber.

Figure 6:
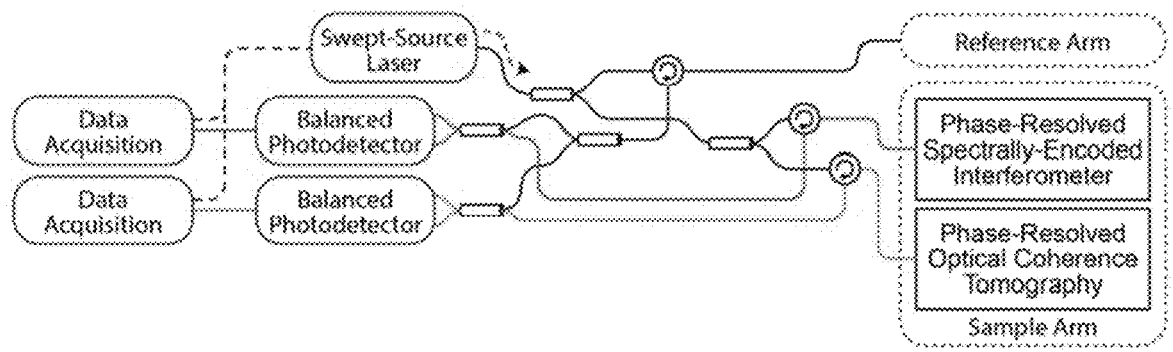
FIG. 6 shows an optical system diagram for a co-registered OCM-imaging and SEIM-imaging system.
Figure 7:
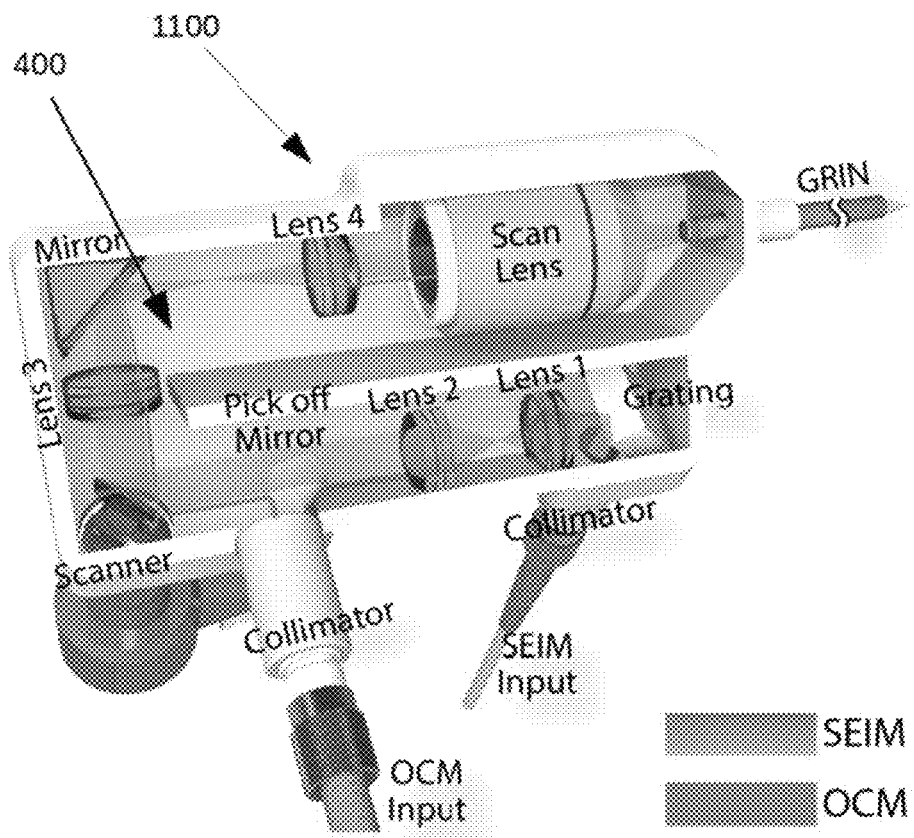
FIG. 7 shows an illustration of a dual-path rigid handheld probe for the system configuration described in FIG. 6.

The invention may further include a position guiding system on the dual-path hand-held probe (1100). The position guiding system may include, but is not limited to, an endoscopic camera. As a non-limiting example shown in FIG. 7, which is based on the system configuration described in FIG. 6, a dual-path hand-held probe (1100) comprises a grating and a 4F optical relay, wherein the hand-held probe spatially disperses the illumination light along a line, thereby providing the fast scan, for SEIM. A galvanometer mirror is used to scan SEIM, providing the slow scan. The light beam enters another 4F optical relay, wherein a scan lens is positioned at the distal end, through which the light will focus into a GRIN rod, wherein the GRIN rod is encased in a stainless tube to provide the insertable portion of the hand-held probe. At the end of the hand-held probe, a mirror may be attached to allow imaging at different anatomical landscapes through the commonly used viewing angles: 0°, 30°, and 45°. The insertable portion of the hand-held probe is removable for the ease of sterilization. Phase information on the deeper tissue (i.e., beneath cilia layer) is obtained for bulk motion removal (i.e., stabilization) and for surface position tracking. OCM will be achieved by coupling a non-dispersed collimated swept-source light into the SEIM optical path by a pick off mirror. This design will allow simultaneous en face SEIM and classic cross-sectional OCM. In addition, OCM structural images will allow tissue surface tracking to guide the imaging probe, and the phase information will be used for bulk motion subtraction to remove tissue motion artifacts. The invention may further include a stabilizing system for the hand-held probe. The stabilizing system may include, but is not limited to, a neuroretractor or an automatic robotic arm system. The invention may further include a de-noise method to extract the bulk motion of in-vivo subject and eliminate it from the PRD measurement of ciliary activity. The bulk motion extraction method may include, but is not limited to measuring the sample movement below the tissue surface, or using a frequency filter to isolate the frequency component of the bulk motion. The method to obtain the below surface movement may include, but is not limited to using the depth resolved PRD algorithm on SEIM or OCM raw data.

Figure 2:
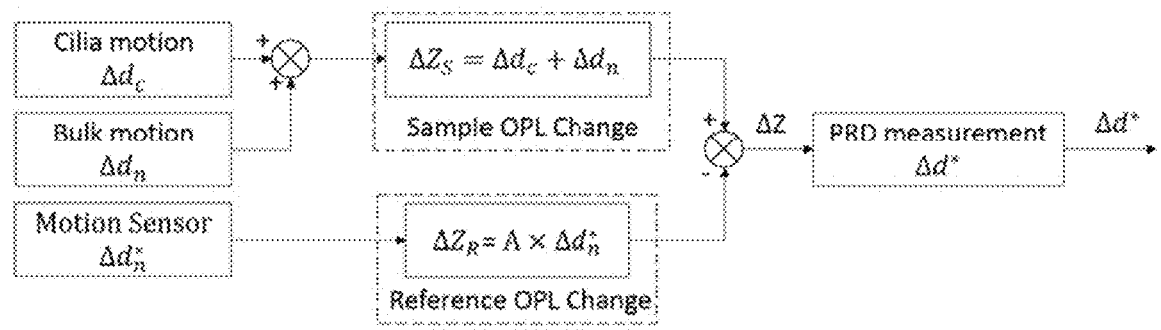
FIG. 2 shows a block diagram of an open loop control system.
Figure 3:
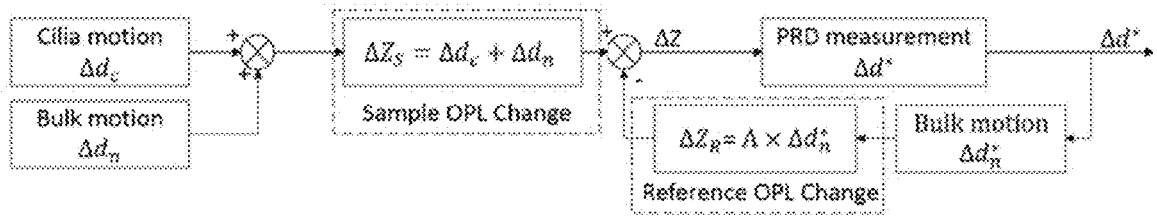
FIG. 3 shows a block diagram of a closed loop control system.

The invention may further include a control system, as in FIG. 2 and FIG. 3, that minimizes the bulk motion induced optical path-length (OPL) difference. As a non-limiting example, the control system may further utilize an open-loop configuration, as in FIG. 2, to cancel the OPL change induced by the bulk movement.

Since both ciliary motion $\Delta d_c$ and bulk motion $\Delta d_n$ can contribute changes to the optical path length (OPL) $Z_S$, it is necessary to eliminate the influence of bulk motion in order to obtain PRD measurement on ciliary motion only. To cancel the bulk motion induced OPL change, we can change the OPL of reference arm $\Delta Z_R$ along with the bulk motion, so that the total OPL change will only depend on ciliary motion. An open loop control system requires an extra motion sensor to measure the bulk motion $\Delta d_n^*$ and an actuator to change the reference arm OPL accordingly.

The control system may further utilize a closed-loop configuration, as in FIG. 3, to cancel the OPL change induced by the bulk movement.

We can further utilize the PRD measurement as the feedback to cancel the bulk motion. It is possible to extract the bulk motion from the PRD measurement because its characteristics are highly different from ciliary motion in term of intensity, frequency, and spatial distribution. Thereby, the control system can use the extracted bulk motion $\Delta d_n^*$ to control the reference OPL change so as to minimize the bulk motion induced OPL change. Prior study integrated a balloon stabilizer on the endoscope to ensure stable measurement. However, the contact between infiltrated balloon and ciliated tissue may affect the ciliary activity and pose a negative impact on the effective of measurement. Plus, the balloon-based solution may increase the overall screening time in the way that images cannot be taken before the balloon is fully infiltrated. Herein, the OPL control system does not need mechanical stabilizer, so that allows for non-contact real time ciliary imaging.

The invention further includes a short-time Fourier-transform based algorithm to obtain volumetric displacement images of ciliated tissue.

Figure 4:
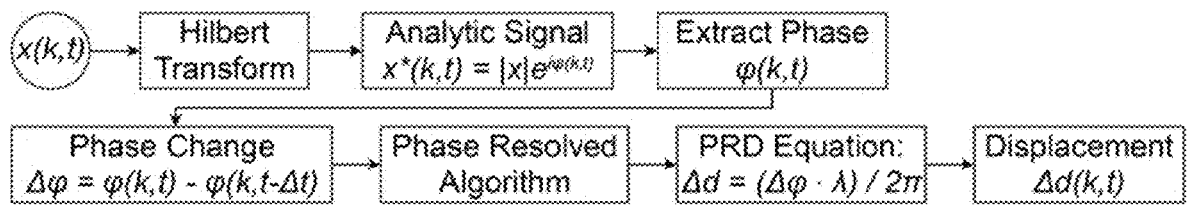
FIG. 4 shows a block diagram to obtain en face displacement information using a PRD-SS-SEIM system. t: time, φ: phase, d: displacement, s: raw signal, x: fast scan axis, z: depth axis, y: slow scan axis.
Figure 5:
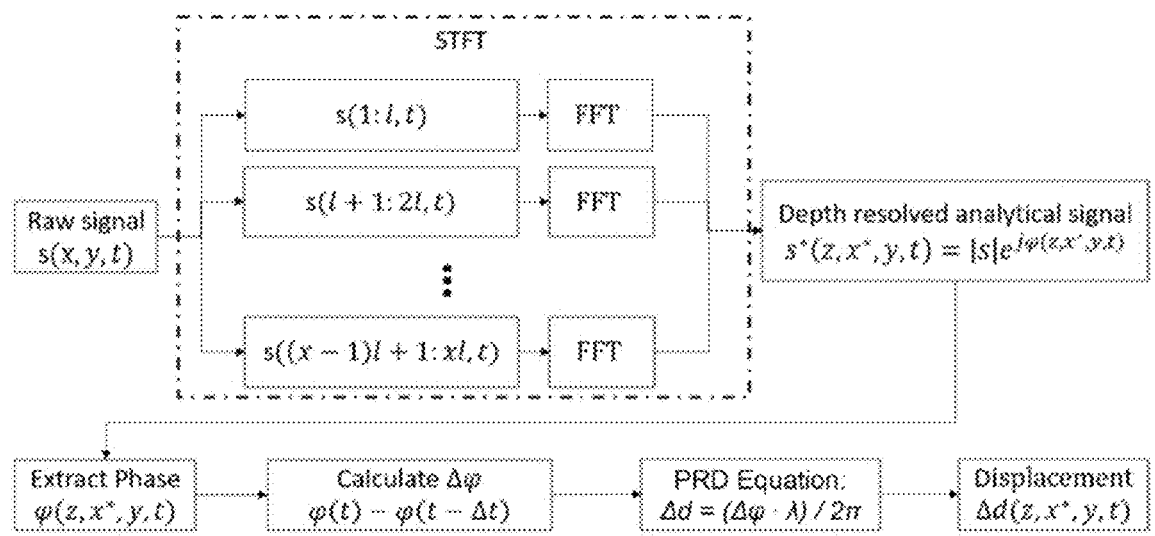
FIG. 5 shows a block diagram to obtain volumetric displacement information using a PRD-SS-SEIM system. t: time, v: phase, d: displacement, s: raw signal, x: fast scan axis, z: depth axis, y: slow scan axis.

FIG. 4 shows the algorithm to obtain en face displacement image from the SEIM raw signal. The raw signal denotes the digitized interferogram at time t. Since different wavelengths are focused in order as a line on the sample, the wavelength, λ, corresponds to the fast scan axis x. The slow scan position y is determined by the galvanometer (402). By using Hilbert transform, we can generate the line's analytical form s* which contains the phase information φ. According to the theory of PRD, sample motion will induce optical path length (OPL) change that is proportional to the phase change over time. Therefore, we can calculate the phase change over time and map out the en face sample displacement $\Delta d$ using the PRD equation.

The invention further include a Hilbert transform based algorithm to obtain the displacement of each pixel within a PRD-SEIM en face image.

Herein, we demonstrate the algorithm to obtain volumetric displacement from SEIM system using PRD algorithm. Like the theory of OCT, the depth resolved displacement information of SEIM data is encoded by the wavelength component of the interferograms. In order to obtain the volumetric information, we can perform short time Fourier transform (STFT) on the raw signal to obtain the depth resolved signal s*. The window size I determines how many successive fast scans are used to obtain one depth resolved signal, and the fast axis coordinates is transformed to x*=⌊x/l⌋ accordingly. Eventually, with the phase information at each spatial location (x*, y, z), we will be able to generate the volumetric displacement using the PRD equations.

The invention may further include a processing algorithm to map the spatial cilia beating frequency and cilia beating pattern. The processing algorithm may further obtain the spatial CBF using Fourier transform on the spatial-temporal en face images. The processing algorithm may further obtain instantaneous spatial beating frequency and phase of the surface ciliary activity using Hilbert transform analysis. The invention may further include a real time imaging processing method for PRD-SEIM system. The real time imaging processing method may include, but is not limited to, a parallel processing algorithm based on multiple graphic processing units (GPU).

Prior study utilized LabVIEW 2013 to register and log the Doppler spectrally encoded data, but cannot generate real time displacement images. Herein, we describe an embodiment of the multiple GPU processing framework for real time PRD-SEIM data processing. The CPU registers the raw signal in a buffer in the order of B-Scan frames. The CPU Thread 0 copies the buffered SEIM data to the GPU buffers. This embodiment further creates three CPU threads to control three separated GPUs that integrates the paralleled PRD-SEIM processing algorithm. The threads process the B-scans in a preemptive manner and the processed B-scans will not be considered again. Eventually, the processed data will be transferred back from GPU to CPU for display and logging.

The invention may further include a phase stable laser to ensure accurate PRD measurement. The phase stable laser may include, but is not limited to, an akinetic swept source laser.

In one embodiment the present invention features an apparatus for performing phase resolved Doppler swept source spectrally encoded interferometric microscopy. As a non-limiting example, the apparatus may comprise: a swept source laser (100), an optical coupler (201), a laser collimator (206), a diffraction grating (401), a plurality of lenses and mirrors (400), a detector (600), and a processor (900).

In some embodiments, the swept source laser (100) may be capable of generating a beam of laser light at a time-varying range of wavelengths at a repeated interval. In some embodiments, the optical coupler (201) may be capable of dividing the laser beam into a sample arm (301) and a reference arm (302). In some embodiments, the laser collimator (206) may be capable of producing a collimated beam of laser light, disposed to receive the light beam from the sample arm (301) of the swept source laser (100). In some embodiments, the diffraction grating (401) may be disposed to receive the collimated beam from the sample arm (301), capable of diffracting light at varying angles according to wavelength, wherein the swept source laser (100) light is diffracted in varying directions over time as the light sweeps through the repeated interval, wherein the resulting sweep of light comprises a fast scan in a first direction.

In some embodiments, the plurality of lenses and mirrors (400) may be disposed to direct the diffracted sweep of light onto a tissue sample (500), comprising at least one galvanometer mirror (402), wherein the galvanometer mirror (402) moves so as to reflect the light in a second direction (702) comprising a slow scan, wherein the second direction (702) is perpendicular to the first direction (701), wherein the light is reflected back from the tissue sample (500) through the plurality of lenses and mirrors (400). In some embodiments, the detector (600) may be disposed to receive light reflected from the sample arm (301) and from the reference arm (302), wherein the light returned from the sample arm (301) and the reference arm (302) combine to form an interference pattern.

In some embodiments, the processor (900) may be operatively connected to the swept source laser (100), the at least one galvanometer mirror (402), and the detector (600). In some embodiments, the processor (900) may be configured to execute computer-readable instructions. As a non-limiting example, the instructions may comprise: (i) receiving triggers from the swept source laser (100) to begin an acquisition during which the laser light is swept across a range of wavelengths, wherein the laser beam sweeps across the tissue sample (500) while varying its frequency in the first direction (701); (ii) controlling the galvanometer mirror (402) to rotate so as to move the beam in the second direction (702); (iii) receiving an interference pattern from the balanced detector (600); (iv) computing the Doppler shift of the light reflected from the tissue sample (500) from the interference pattern; (v) computing the displacement velocity of tissue sample (500) from the Doppler shift; (vi) repeating steps (iii)-(v) as the swept source laser (100) sweeps through the time varying range of wavelengths; (vii) repeating steps (i)-(vi) as the galvanometer mirror (402) is moved in the second direction (702); and (viii) generating a two-dimensional image by assigning the computed velocity to a pixel, wherein the location of the pixel corresponds to a specific position along the first direction (701) and the second direction (702) coordinate axes.

In some embodiments, the apparatus may feature a dichroic mirror (403) to split the beam spectrally for co-registration of OCM and SEIM data. In some embodiments, splitting the beam spectrally for co-registration may provide for more robust co-registration than if the beam had been split spatially. In some embodiments, the apparatus may feature a 4F lens system as an optical relay configured to flatten the image. In some embodiments, the apparatus may feature a microscopic lens system (407) configured to allow for high lateral resolution imaging.

EXAMPLE

The following is a non-limiting example of the present invention. It is to be understood that said example is not intended to limit the present invention in any way. Equivalents or substitutes are within the scope of the present invention.

The present invention features the first PRD-SEIM system to do real time en face imaging of ciliated tissue. This invention has been developed and validated by two trachea samples and one oviduct sample ex-vivo, where the microscopic surface dynamic of these tissues were visualized at different temperatures and drug applications.

The invention features a PRD-SEIM method of measuring and quantifying the spatial ciliary beating frequency of ex-vivo rabbit trachea. This technology offers high resolution, high speed and high sensitivity en face image of tissue structure and displacement. To be specific, the PRD algorithm allows for nanometer displacement sensitivity, ensures accurate measurement of the microscopic ciliary movement. Furthermore, swept source laser based SEIM system enables micron scale pixel resolution and real time imaging, which are essential to visualize the periodic ciliary activity. In addition, the invention is non-invasive since SEIM can be readily used for endoscopic imaging in-vivo according to previous publications. The technology allows real time visualization and analysis of the ciliary activity both spatially and temporally with adaptability for clinical translation and in-vivo analysis.

The Spectrally Encoded Microscopy System Design

The SS-SEIM system is developed using a vertical-cavity surface-emitting laser (VCSEL) based swept source OCT system, wherein the present invention is not limited to swept source OCT, wherein the present invention is also applicable to spectrometer-based systems. The center wavelength of the system is 1.3 um, and the A-line rate is 100 kHz, wherein the term A-line rate denotes the rate of advance of the slow scan index, per unit time, of rasterizing process. The scan speed is not limited to 100 kHz swept source and 91 fps; in some embodiments, the scan speed may vary up to 10 MHz depending on the performance of the light source and the frame rate may vary up to 20,000 fps depending on the performance of the scanner. The lateral resolution and displacement sensitivity are measured to be 1.2 μm and 0.3 nm, respectively. The sample arm (301) is replaced by a spectrally encoded microscopy setup, which allows for simultaneous sample illumination with a single mode fiber input. The light in the sample arm (301) is first collimated and diffracted by the diffraction gratings, yielding a line pattern as the laser sweeps through its full bandwidth. The 1-D galvanometer mirror G1 (402) scans the wavelength encoded line of light in its perpendicular direction to produce en face optical imaging. Two optical relays are employed to center the line of light on to the galvanometer mirror (402) and the back focal point of the objective lens (407), hence ensuring a flat scanning plane on the tissue sample (500) surface. After, a focused line is illuminated on the tissue sample (500) through the objective lens (407), where different wavelengths are focused on different locations of the tissue sample (500) based on their diffraction angles. The collected back scattered light interferes with the light from the reference arm (302) to form an interferogram which is detected by a balance detector (600). The system is capable of real time en face displacement imaging at up to 100 fps with 1000 A-lines per image and 2048 pixels per A-line, providing a FOV of approximately 480 μm×750 μm. The system schematic is illustrated in FIG. 1A.

Ex Vivo Tissue Preparation

Rabbit tracheal samples were harvested from freshly euthanized male New Zealand white rabbits under the approval of the Animal Care and Use Committee (IACUC) at UC Irvine. The tissues were immediately submerged in Hanks Balanced Salt Solution (HBSS) and kept at room temperature of approximately 23° C. Soft tissue was carefully dissected from the outer surface of the trachea to ensure an even surface for imaging. The tissue was cut along the long axis of the trachea to reveal the mucosal surface for imaging, and then secured down with pins onto a silicone-lined petri dish. A layer of HBSS was added to the dish to mimic the natural tissue environment and minimize disruption of ciliary motion. Finally, the sample was moved to the imaging stage where it was placed on a temperature-controlled hot plate for temperature regulation during imaging. For lidocaine treatment, 2% lidocaine was added to the sample while submerged in HBSS, and imaging was performed after 5 minutes. For albuterol experiments, the sample was kept in 2 ml HBSS buffer with 0.3% albuterol, and imaging was performed approximately 1 minute after drug application.

Processing Algorithm

Figure 1C:
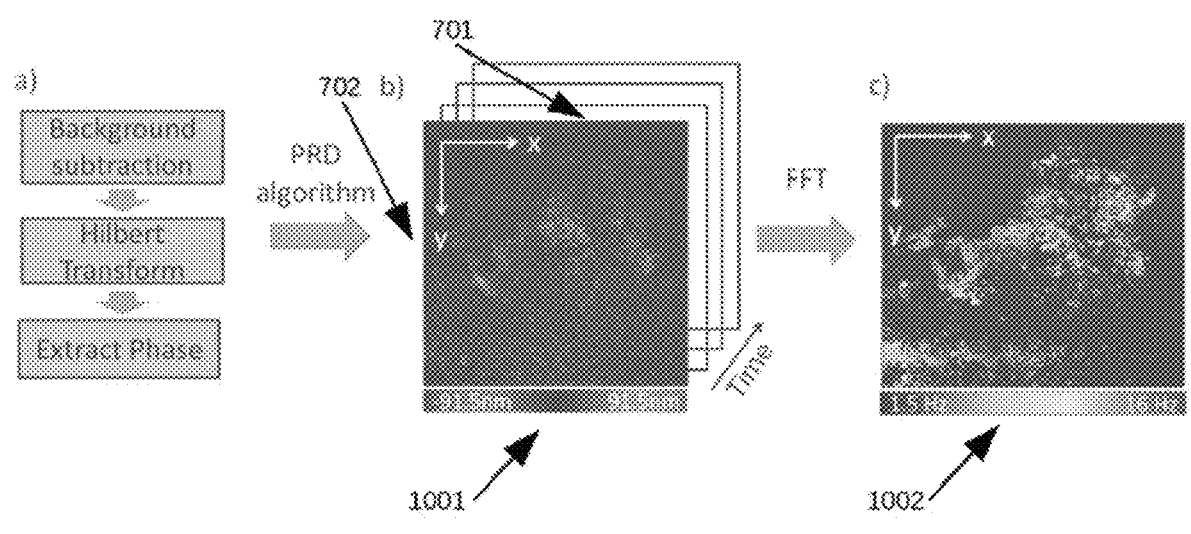
FIG. 1C shows a processing flow chart for obtaining spatial temporal ciliary activity and spatial CBF. a) algorithm to achieve phase value at each imaging point. b) Axial displacement images spaced at same time interval. c) 2-D CBF map.
Figure 9:
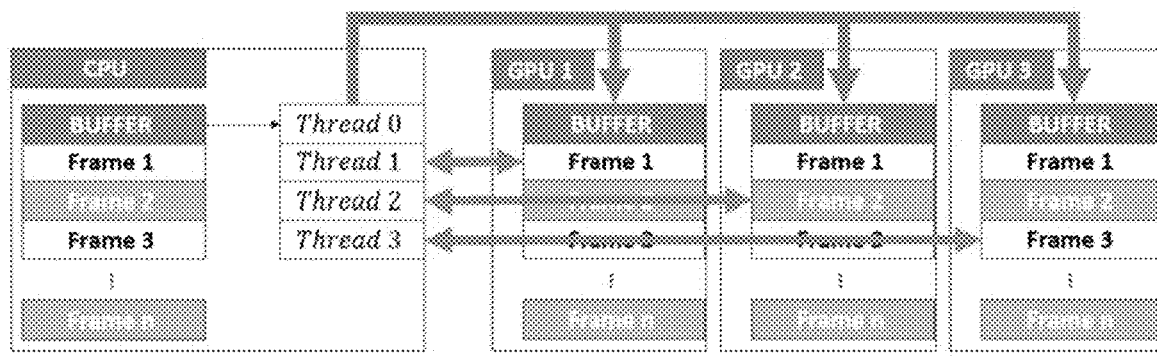
FIG. 9 shows a schematic of a multi-GPU processing framework for real time PRD-SEIM.

According to PRD, the particle displacement ΔZ can be measured by analyzing the temporal phase changes of its corresponding interference component. Under the context of SEIM imaging, the position of the particle is indexed by the wavelength due to the laterally dispersed tissue sample (500) illumination, and thereby the PRD equation for the SEIM system can be modified as below.

$$\Delta Z(k,t) = \varphi(k, t+\Delta t) - \varphi(k,t)/k \qquad \text{Equation 1}$$

wherein k denotes the wavenumber of the illumination on the particle of interest, wherein the wavenumber k is related to wavelength λ as πλ, and Δt represents the sampling interval that was determined by the frame rate. For the purpose of investigating the temporal dynamics of ciliated tissue, the region of interest was oversampled at 91 fps, wherein the term fps denotes "frames per second". The instantaneous phase, φ(x, t), was derived from the Hilbert transformation on the spectral interference fringe. By performing the algorithm on consecutive en face images, spatial-temporal ciliary dynamics can be visualized. The spatial beating frequency of cilia was mapped out by extracting the beating frequency from the spatial-temporal data through a Fourier transformation over time, as in FIG. 1C. The flow chart of the processing algorithm is shown in FIG. 1C. The PRD based processing algorithm and SEM system control program are implemented in custom C++ software, and accelerated by graphics processing unit (GPU), as in FIG. 9, to provide on face displacement images in real time.

Results:

During imaging, the line scan was made to focus on the cilia layer on the top surface of the trachea sample. In addition to synchronized ciliary motion, some random ciliary movements were also observed at certain parts of the sample. For the purpose of measuring the CBF, we focus on the regions with synchronized motion. The ciliary motion is visualized in real-time and the region of interest can be identified and imaged efficiently.

Spatially Mapped CBF vs. Temperature

Figure 10:
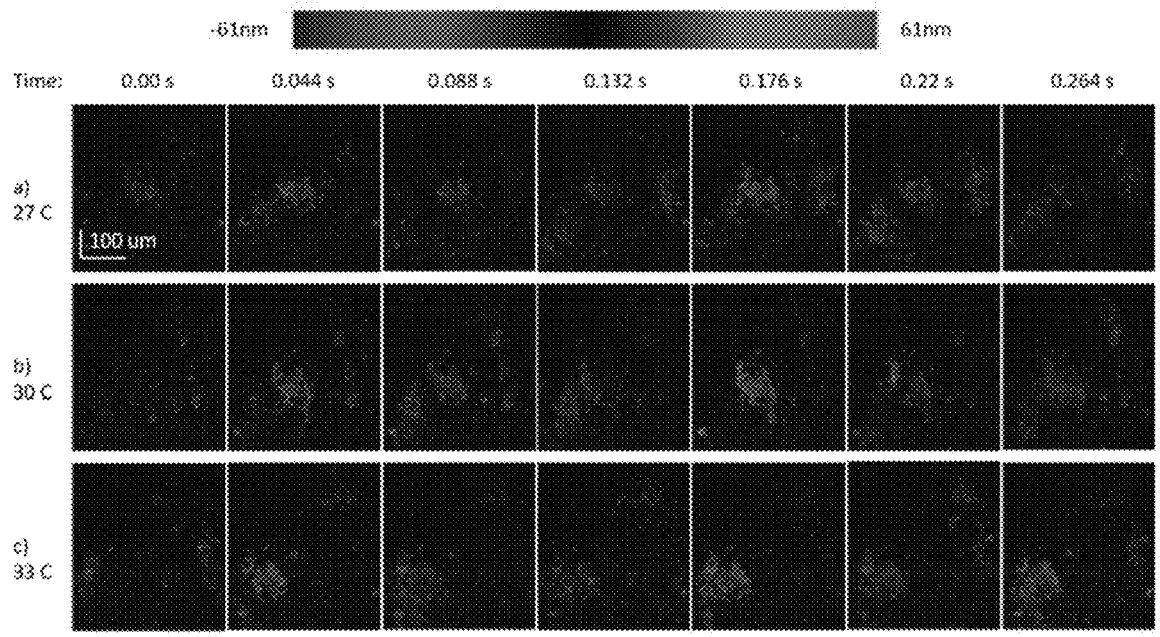
FIG. 10 shows cilia motion at different temperature. a) Synchronized cilia cycle from 0 to 0.2 s at 27° C., b) at 30° C., c) at 33° C.

The tracheal sample was acquired as described in the Ex-vivo Tissue Preparation section and a region with synchronized ciliary motion was identified. SEIM en face imaging was done while increasing the temperature of the sample from room temperature, about 25° C., to 33° C. The raw line-scan Doppler SEIM images are shown in FIG. 10, where the same area of interest is imaged at 27° C., 30° C., and 33° C., respectively. Different colors correspond to the change in the phase amplitude and the direction of the ciliary motion, which is directly proportional to the velocity of the motion. For different temperatures, the time at which the cilia complete a single power stroke cycle can be distinguished. The duration of the phase cycle can be estimated to be about 0.132 s for 27° C., 0.11 s for 30° C., and 0.088 s for 33° C. These results show that the CBF increases with temperature.

Figure 11:
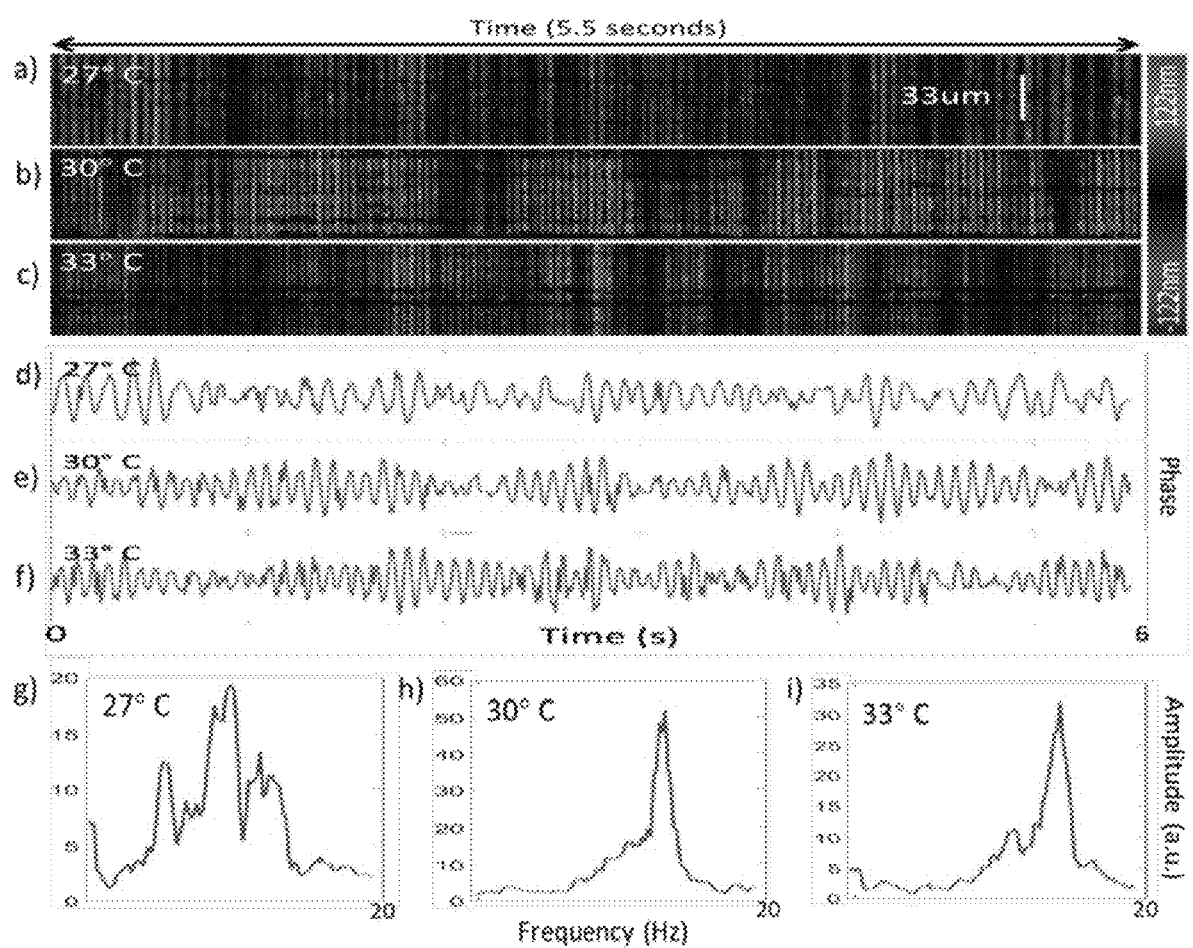
FIG. 11 shows CBF measurements at single location on synchronized cilia, a-c) raw phase data over depth, d-f) mean phase plot of raw data, g-) Frequency distribution after FFT.

Since the spatially encoded data is continuously collected over 6 seconds, the temporal data can also be extracted. The temporal profile, or M-mode, at each spatial location can be measured along the depth direction. It is important to note that the line scan system has advantages in visualizing lateral spatial and temporal information, but sacrifices depth information and can only image superficial structures. However, for thin samples like cilia, tens of microns in depth are more than sufficient. An example of the temporal profile at one line under the 3 temperature conditions is presented in FIG. 11, rows a through c. The phase is averaged across the vertical axis of a through c and drawn out in FIG. 11, rows d through f. Although the phase amplitude varies depending on the angular fluctuations of the sample and noise, the CBF is mostly consistent. In order to quantitatively determine the CBF at that particular location, a FFT is performed on the phase plot to yield the frequency plots in FIG. 11, row g. The peak frequency occurs at 9 Hz, 12 Hz, and 13 Hz for the 27° C., 30° C., and 33° C. cilia samples respectively.

Figure 12:
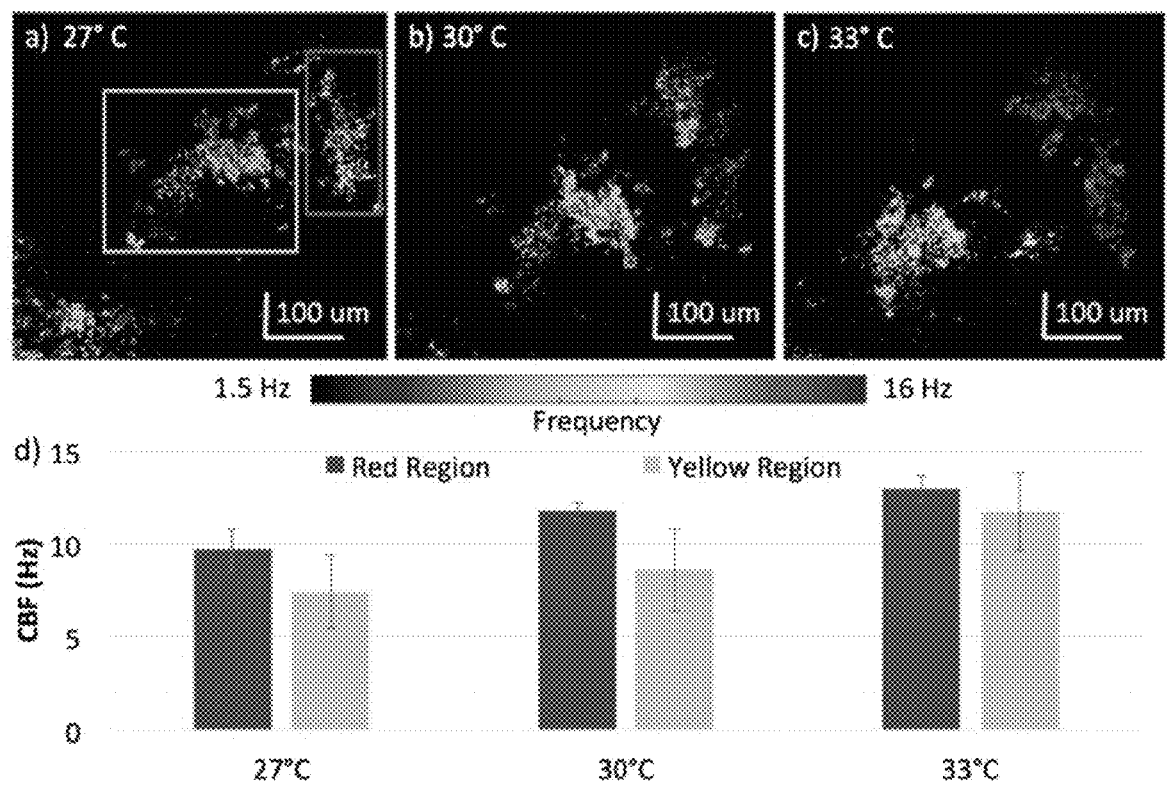
FIG. 12 shows the spatial distribution of CBF with changes in temperature. a) at 27° C., b) at 30° C., c) at 33° C. with the same corresponding region, d) CBF analysis of yellow and red regions.

With the same data processing method, the temporal data is analyzed at each spatial location to yield the spatially coded CBF maps as shown in FIG. 12 for the three temperatures, respectively. The same region was imaged for all three conditions, where there appeared to be 2 separate bodies of synchronized cilia, marked by the yellow and red boxes. Small changes in the CBF can be observed between the two spatial regions at each temperature. With the increase in temperature, the CBF of all cilia increased as expected, and the means and standard deviations of both regions at each temperature have been plotted in FIG. 12, row d. The mean values ranged between 7.4 Hz and 13 Hz, all reasonable values for mammalian CBF. A general upward trend can be concluded between the CBF and the temperature.

Spatially Mapped CBF vs. Lidocaine Application

Figure 14:
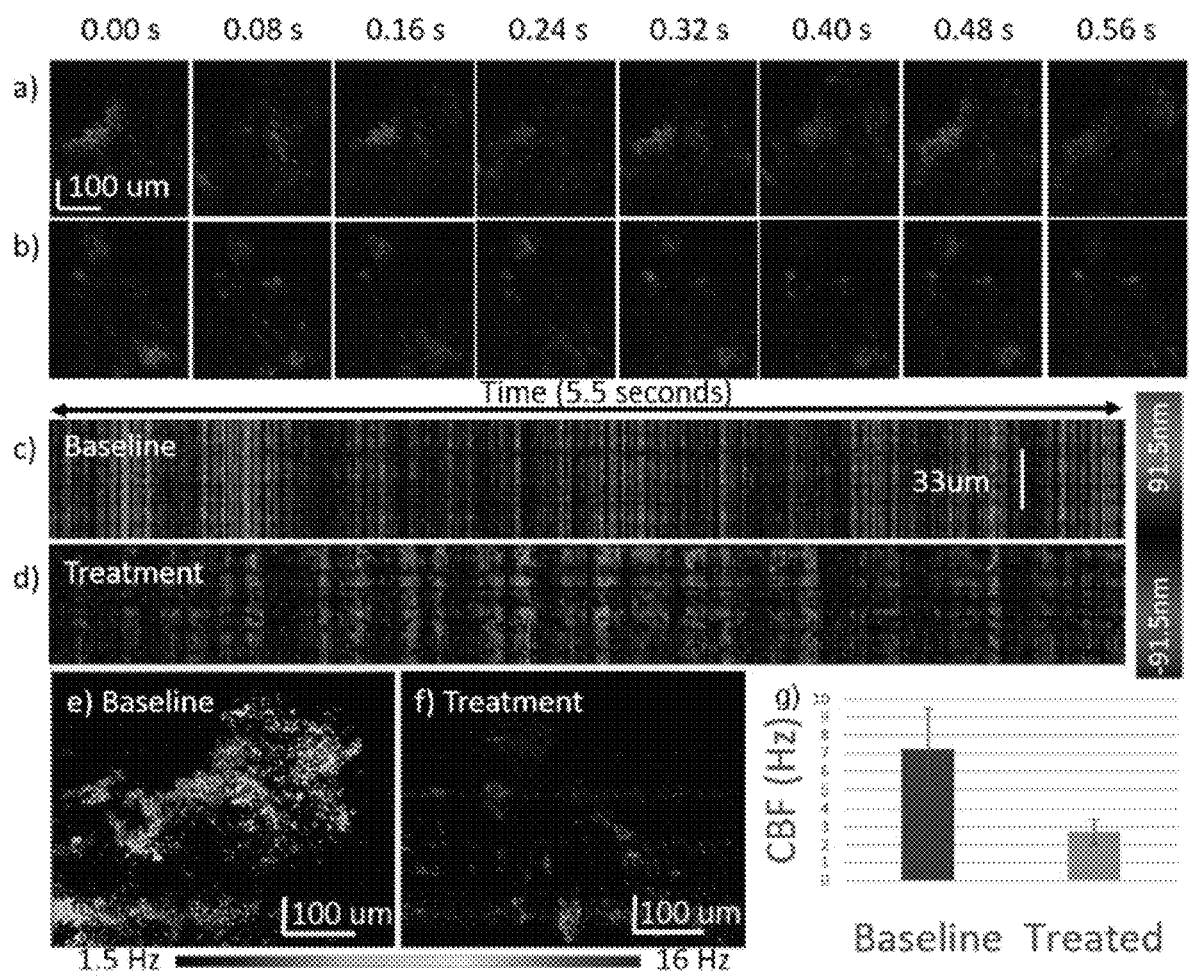
FIG. 14 shows the effect of 2% lidocaine treatment on CBF. a) Synchronized cilia cycle from 0 to 0.2 s for baseline sample at 23 C. b) Synchronized cilia cycle from 0 to 0.2 s for treatment sample at 23 C. c) Raw phase data of baseline data. b) Raw phase data after treatment. Note that most of the cilia were no longer active after treatment, and a small region of active cilia was used for analysis. e) Spatial distribution of CBF for baseline sample. f) Spatial distribution of CBF for treatment sample. g) CBF analysis of entire region.
Figure 15:
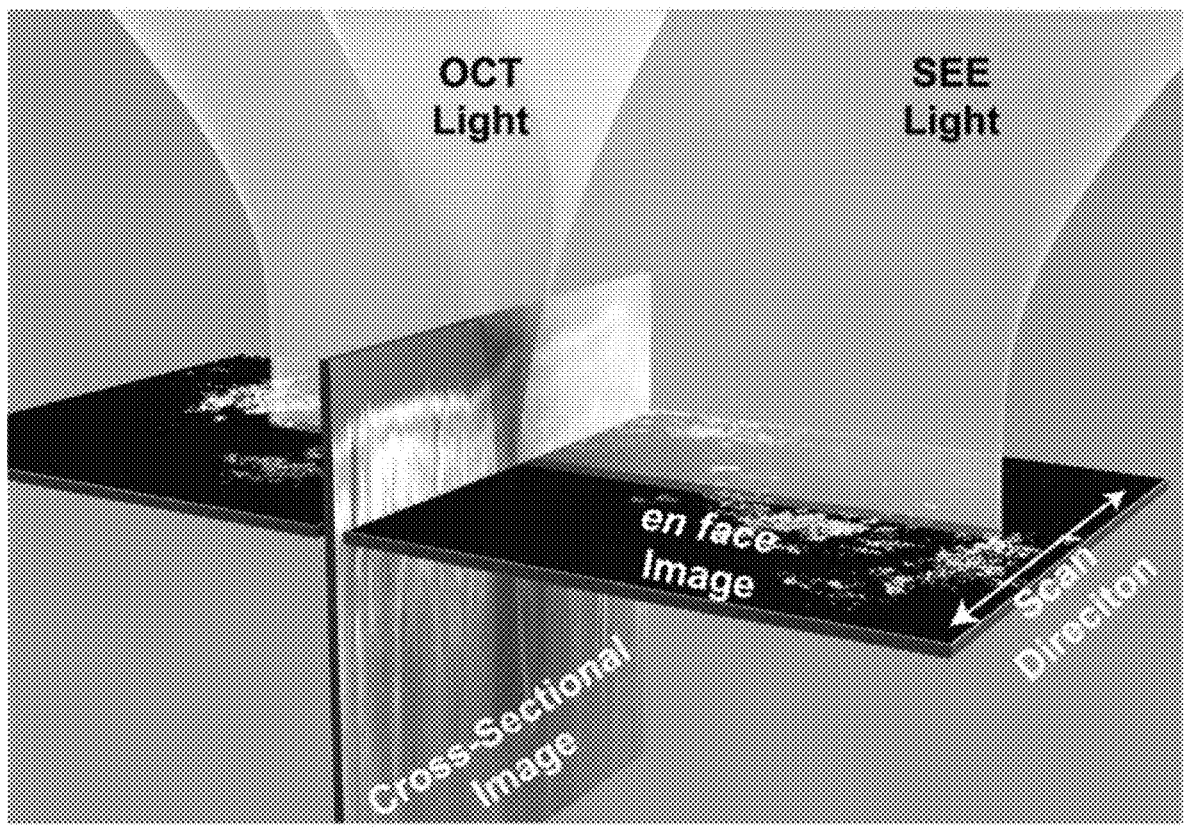
FIG. 15 shows a schematic of PR-SEIM (blue) and OCM (pink) integration. En face and cross-sectional images are acquired simultaneously, in which the OCM images enable surface tracking ability and allow for background bulk motion and other phase noise removal.

For the next experiment, the effects of lidocaine administration were studied. In general, lidocaine is a local anesthetic that is expected to significantly slow down ciliary motion and mucus transport. For this experiment, all samples were kept at 27° C. As described in the methods section, 2% lidocaine was applied to the sample and imaging took place after 5 minutes. The raw en face images for the baseline measurement and after lidocaine application are shown in FIG. 14, rows a and b, respectively. While the baseline cilia completed a full power stroke cycle in approximately 0.14 s, the lidocaine-treated cilia is not even halfway through the cycle in the same amount of time. Again, the temporal or M-mode data is plotted at every spatial location, yielding in the examples shown in FIG. 14, rows c and d for the baseline and lidocaine-treated cilia, respectively. From the temporal data, it is evident that the frequency decreased significantly after lidocaine administration. The displacement plot was generated using the average phase over the entire depth and FFT was performed to calculate the frequency peak at each location. Finally, the spatial map can be visualized in FIG. 14, rows e and f, which are before and after drug administration respectively. The mean and standard deviation for the baseline and treatment data were calculated using the CBF from each spatial location where cilia is present, and plotted in FIG. 14, row g. The mean CBF before treatment was 7.2 Hz and decreased to 2.7 Hz after treatment. As shown in the spatial map, many of the cilia stopped moving altogether after lidocaine was applied, while others merely slowed down. Only the active cilia were taken into account when calculating the mean CBF and standard deviation.

Spatially Mapped CBF Vs. Albuterol Treatment

Figure 13:
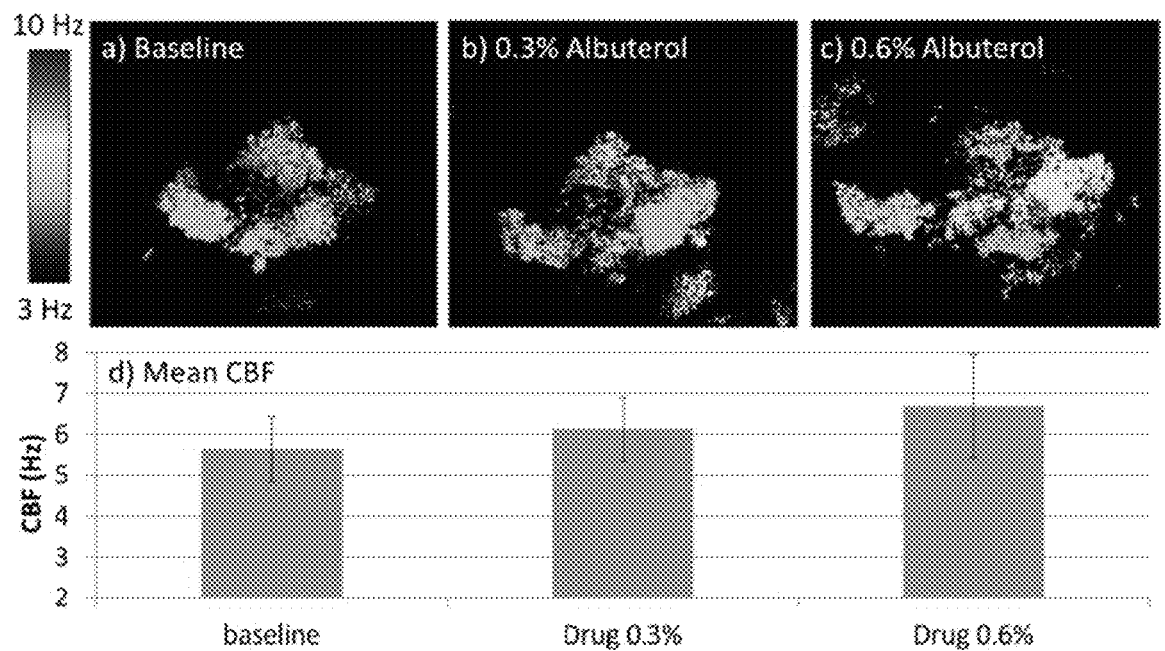
FIG. 13 shows the effect of albuterol treatment on CBF. a) Spatial distribution of CBF for baseline. b) Spatial distribution of CBF for sample treated with 0.3% albuterol. c) Spatial distribution of CBF for sample treated with 0.6% albuterol. d) CBF analysis of entire region.

Ciliary activity in response to albuterol, which is commonly used to increase respiratory function, was also investigated to further verify the system effectiveness. According to previous reports about the effects of albuterol on ciliary tissue, CBF is expected to increase with the introduction of the drug. Similar to the lidocaine experiment, a rabbit trachea sample is kept at room temperature and the baseline data is first recorded when the sample is placed in HBSS buffer only. Then the buffer is replaced with a 0.3% albuterol solution as mentioned in the methods section, and imaging was performed after approximately 1 minute. As shown in FIG. 13, the spatial CBF for the experimental group increased across the region of interest from a baseline of 5.64 Hz to 6.13 Hz. We then added more albuterol to the buffer to achieve a 0.6% drug concentration. As expected, the overall CBF increased again to 6.7 Hz. In addition, more regions of ciliated cells are activated and contribute to a more synchronized ciliary activity within the same imaging area. The mean and standard deviation values are calculated and plotted in FIG. 13, row d.

DISCUSSION & CONCLUSION

CBF is one of the most important indicators of respiratory health, and studying the mechanisms of ciliary motion is crucial in understanding diseases of the airway. The currently available methods mostly focus on ex-vivo microscopy and high-speed camera imaging, which do not offer a realistic examination of the CBF in its natural environment. In addition, previous methods of CBF analysis using temporal coded data are limited to M-mode imaging with limited spatial mapping. Therefore, this study aims to visualize and analyze the CBF both spatially and temporally with adaptability for clinical translation and in-vivo analysis.

For this initial feasibility study, variations in the CBF were observed within a spatial region. While some differences in CBF are expected across a sample, it would be worthwhile to more closely analyze the origin of these variations to better understand ciliary motion. It was also obvious that some cilia were beginning to degrade and were no longer moving in a synchronized manner with each other. These randomly moving cilia contributed to noise within the sample and the measured CBF. Future in-vivo studies can help better explain the loss of synchronicity and spatial changes in CBF by eliminating the tissue degradation and freshness factors.

The two primary challenges of translating this technology to in-vivo studies are the noise factor and the clinical adaptability of the scanner. Bulk motion from breathing is expected to have a large impact on the data. However, since noise from breathing is largely characterized by a low frequency bulk movement, frequency analysis can be utilized to eliminate these factors. The current system sample arm and scanner unit is bulky and unsuitable for in-vivo studies. However, a handheld probe (1200)-based design is currently under fabrication to ensure clinical adaptability in the next study.

The present invention features a novel method of spatially mapping the CBF and ciliary motion with high speed, high resolution Doppler SEIM. With this line-scan system, where the term line scan herein refers to SEIM, we are able to acquire real-time on face images of the cilia and analyze the synchronicity of the motion. A general trend was observed between increases in the external temperature and increases in the CBF. In addition, the CBF decreased significantly after application of lidocaine and an increasing trend was observed with the introduction of albuterol. The feasibility of using the SS-SEIM technology to map the CBF has been validated across different conditions and the results serve as a stepping stone to our ongoing translation of the technique to in-vivo and clinical studies.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An apparatus for performing phase resolved Doppler swept source spectrally encoded interferometric microscopy, comprising:
   a. a swept source laser (100), capable of generating a beam of laser light at a time-varying range of wavelengths at a repeated interval;
   b. an optical coupler (201), capable of dividing the laser beam into a sample arm (301) and a reference arm (302);
   c. a laser collimator (206), capable of producing a collimated beam of laser light, disposed to receive the light beam from the sample arm (301) of the swept source laser (100);
   d. a diffraction grating (401), disposed to receive the collimated beam from the sample arm (301), capable of diffracting light at varying angles according to wavelength, wherein the swept source laser (100) light is diffracted in varying directions in about proportion to its wavelength over time as the light sweeps through the repeated interval of wavelength, wherein the resulting sweep of light constitutes a fast scan in a first direction (701);
   e. a plurality of lenses and mirrors (400), disposed to direct the diffracted sweep of light onto a tissue sample (500), comprising at least one galvanometer mirror (402), wherein the galvanometer mirror (402) moves so as to reflect the light in a second direction (702) comprising a slow scan, wherein the second direction (702) is about perpendicular to the first direction (701), wherein the light is reflected back from the tissue sample (500) in a direction about perpendicular to both the first direction (701) and the second direction (702) through the plurality of lenses and mirrors (400);
   f. a detector (600), disposed to receive light reflected from the sample arm (301) and from the reference arm (302), wherein the light returned from the sample arm (301) and the reference arm (302) combine to form an interference pattern; and
   g. a processor (900), operatively connected to the swept source laser (100), the at-least-one galvanometer mirror (402), and the detector (600), wherein the processor (900) is configured to execute computer-readable instructions comprising:
      i. triggering the swept source laser (100) to begin a fast scan, during which the swept source laser (100), which triggers the processor (900), sweeps across a range of; wherein accordingly the laser beam main lobe sweeps across the tissue sample (500) in the first direction (701) due to the action of the diffraction grating (401);
      ii. controlling the galvanometer mirror (402) to rotate the mirror so as to move the beam in the second direction (702);
      iii. receiving an interference pattern from the balanced detector (600);
      iv. computing the Doppler shift of the light reflected from the tissue sample (500) from the interference pattern;
      v. computing the velocity of the tissue sample (500) from the Doppler shift;
      vi. repeating steps (iii)-(v) as the laser sweeps through the time varying range of wavelengths;
      vii. repeating steps (i)-(vi) as the galvanometer mirror (402) is moved in the second direction (702);
      viii. generating a two-dimensional image by assigning the computed velocity (response variable) to a pixel, wherein the location of the pixel corresponds to a specific position along the first direction (701) and the second direction (702) coordinate axes.

2. The apparatus of claim 1, wherein the apparatus features a dichroic mirror (403) to split the beam spectrally for co-registration of OCM and SEIM data.

3. The apparatus of claim 2, wherein splitting the beam spectrally for co-registration provides for more robust co-registration than if the beam had been split spatially.

4. The apparatus of claim 1, wherein the apparatus features a 4F lens system configured to flatten the image.

5. The apparatus of claim 1, wherein the apparatus features a microscopic lens system configured to allow for high lateral resolution imaging.

6. The apparatus of claim 1, wherein the bulk motion of the tissue sample (500) under study is removed from interfering with the desired cilia-field motion analysis via (a) an open-loop control system that modulates the reference arm (302) optical path length, or (b) a closed-loop control system that modulates the reference arm (302) optical path length.

7. The apparatus of claim 2, wherein the plurality of lenses and mirrors (400) reside optically within a dual-path handheld endoscopic probe (1100).

8. The apparatus of claim 1, wherein a phase-stable laser replaces the swept source laser (100), wherein the phase-stable laser may include an akinetic swept source laser.

9. The apparatus of claim 1, comprising a multiple GPU framework for real-time data processing, wherein the data processing is PRD-SEIM, OCM, or combination thereof.

10. The apparatus of claim 1, comprising further processing involving Fourier and Hilbert transform techniques, wherein the apparatus may employ parallel processing.

11. The apparatus of claim 1, using a Hilbert transform technique to obtain the displacement of each pixel, and using a short-time Fourier transform technique to obtain volumetric displacement.

12. The apparatus of claim 7, wherein optionally the GRIN rod is embodied by a fiber bundle to achieve a flexible endoscope.

13. The apparatus of claim 1, wherein the PRD measurement participates in a closed-loop control system to cancel the effects of bulk motion.

14. The apparatus of claim 1, comprising a position guiding system, such as an endoscope, that aids in steering the objective lens (407).

15. The apparatus of claim 1, comprising a stabilizing system, such as a neuroretractor or an automatic robotic arm, that stabilizes the hand-held probe (1200).

16. The apparatus of claim 1, comprising a de-noise method to extract the bulk motion of in-vivo subject and eliminate it from ciliary activity; wherein the de-noise method may comprise measuring the sample movement below the tissue sample (500) surface; wherein the de-noise method may comprise using a frequency filter to isolate the frequency component of the bulk motion; wherein the method to obtain the below-surface movement may include, but is not limited to, using the depth-resolved PRD algorithm on SEIM raw data or OCM raw data.

17. The apparatus of claim 1, comprising a SEIM handheld endoscopic probe (1200).

18. The apparatus of claim 17, wherein optionally the GRIN rod is embodied by a fiber bundle to achieve a flexible endoscope.

19. The apparatus of claim 1, wherein the galvanometer mirror (402) is embodied by a microelectromechanical mirror; or a resonance scanner mirror.

20. The apparatus of claim 1, wherein optionally the VCSEL (100) is embodied by a broadband continuous-wave laser; wherein optionally the reference arm (302) is embodied by a spectrometer.

* * * * *